US00PP09438P

United States Patent [19]

Doyle

[11] Patent Number: Plant 9,438

[45] Date of Patent: Jan. 23, 1996

[54] PEACH TREE 'AUTUMN FLAME'

[76] Inventor: James F. Doyle, 7685 N. Thompson Ave., Clovis, Calif. 93611-9016

[21] Appl. No.: 371,034

[22] Filed: Jan. 10, 1995

[51] Int. Cl.[6] ..... A01H 5/00

[52] U.S. Cl. ..... Plt./43.2

[58] Field of Search ..... Plt./43.2

*Primary Examiner*—James R. Feyrer

*Attorney, Agent, or Firm*—Wells, St. John, Roberts, Gregory & Matkin

[57] ABSTRACT

A new and distinct variety of peach tree demoninated varietally as Autumn Flame and which is characterized as to novelty by a date of maturity for commercial harvesting and shipment of approximately September 4 through September 20 under the ecological conditions prevailing in the San Joaquin Valley of central California.

1 Drawing Sheet

BACKGROUND OF THE VARIETY

The present invention relates to a new and distinct variety of peach tree which has been denominated varietally as Autumn Flame, and more particularly to such a peach tree which bears an attractive, highly colored fruit which is ripe for harvesting and shipment from approximately September 4 through September 20 under the ecological conditions prevailing in the San Joaquin Valley of Central California, the present variety being mature for harvesting and shipment at a time in the season when few peach varieties having the same distinctive coloration exists.

It has long been known that the marketability of peaches can be influenced to some degree by numerous factors including their respective dates of harvest, and shipment, as well as their individual external appearance. The Autumn Flame peach tree is noteworthy, as noted above, in producing a highly colored, attractive, late season fruit which is ripe for commerical harvesting and shipment between September 4 and September 20 under the ecological conditions prevailing in the San Joaquin Valley of Central California. Further, the fruit produced by the subject variety is noteworthy for its excellent taste, firm texture and its freestone nature.

ORIGIN AND ASEXUAL REPRODUCTION OF THE NEW VARIETY

The inventor has endeavored, through the years, to develop various improved varieties of fruit trees for the agricultural industry. In this regard, the inventor began, in 1984, a process of developing a new peach tree variety which would produce a highly colored fruit that would mature after the second week of August when few varieties having an attractive red coloration exists. More specifically, the inventor cross pollinated two known varieties of peach trees in an effort to develop the new variety. In particular, the inventor cross pollinated two experimental peach tree selections which have been identified by the alpha numeric designation A48-70 and 1-14S-28, respectively. These trees are proprietary trees and are not commercially available. In this regard, the peach tree identified as A48-70 produces a highly colored peach and is of unknown parentage. This particular tree (A48-70) produces fruit which are mature for harvesting and shipment during the first week of August. Further, the peach tree identified as 1-14S-28 produces fruit which are more modestly colored, and was derived from a cross pollination of the O'Henry peach tree (U.S. Plant Pat. No. 2,964) and the Fairtime peach tree (unpatented). The Fairtime peach tree was developed by the USDA and was released in the early 1970's. This variety produces relatively large, good quality fruit, but the color of same is considered poor. Further, the Fairtime peach tree produces fruit which are ripe for harvesting and shipment in late August in the San Joaquin Valley in Central California. In addition to the foregoing, the peach tree identified by the designation 1-14S-28 matures, and is ripe for harvesting and shipment during the second week of September in the San Joaquin Valley of Central California. The inventor made this cross pollination during the spring of 1988. Hybrid seeds derived from this cross pollination were collected in the fall of 1988. Hybrid seeds were later transferred to the Burchell Nursery, Inc. growing grounds near Oakdale, Calif. in November of 1988 where they were subsequently planted.

These same hybrid seeds sprouted and grew through the 1989 growing season at Oakdale, Calif. At that time, the one-year old seedlings were removed from this growing ground and transplanted, in the early spring of 1990, to an experimental planting area belonging to the Burchell Nursey, Inc. and which is located at Clovis Avenue and highway 99 near the Town of Fowler, Calif. More specifically, a total of 227 hybrid seedlings were replanted at this location in 1990 where this tree was selected. The first asexual reproduction of the variety occurred in August of 1992 when fall buds were placed in Nemaguard peach root stock. These asexually propagated trees were located at the same experimental planting area located near Fowler, Calif. A second asexual reproduction of the variety occurred in the spring of 1993 in a test planting near Parlier, Calif. In this regard, scions of the same peach tree variety were grafted into three-year old Nemaguard peach root stock. This asexual reproduction resulted in over eight feet of growth during the 1993 growing season. Fruit produced subsequently from these individual grafted trees in September of 1994 were compared with those of the original seedling located at the experimental growing grounds near Fowler, Calif. and it has been determined that the fruit produced from these grafted trees were true in all respects to that of the original seedling.

SUMMARY OF THE NEW VARIETY

The Autumn Flame peach tree is characterized principally as to novelty by producing an attractively colored, high quality, late season peach. In this regard, the present variety of peach tree bears fruit which are ripe for harvesting and shipment beginning approximately the first week in September, that is, about a week after the common commercial variety "Fairtime" (unpatented) and approximately at the same date of maturity with that of the commercial variety "Carnival" (U.S. Plant Pat. No. 2,144). The present variety is distinguishable therefrom in view of its highly attractive red coloration, and further, because it appears suitable for both local markets and for long distance shipping. Additionally, the present variety of peach tree is distinguishable from the other known varieties because its harvest date can continue well into September. In this regard, the fruit produced by these tree have a propensity for being quite firm, and additionally hang well on the trees without premature drop. Moreover, the present peach tree variety appears to be noteworthy in view of its charactistic of delaying maturity to an even later date in September when increased levels of nitrogen fertilizers are applied. As noted above, the present variety has an improved skin blush coloration when compared with either the "Fairtime" or Carnival" peach tree varieties. Additionally, the fruit flavor is considered superior to both of the varieties noted above.

BRIEF DESCRIPTION OF DRAWING

The accompanying drawing is a color photograph of a characteristic twig bearing typical leaves; several leaves showing both the dorsal and ventral coloration thereof; and several mature fruit showing their external coloration sufficiently matured for harvesting and shipment. Additionally, one fruit of the subject variety is dissected in the axial plane to illustrate the flesh and stone characteristics thereof, all of the subject variety.

DETAILED DESCRIPTION

Referring more specifically to the pomological details of this new and distinct variety of peach tree, the following has been observed under the ecological conditions prevailing at the orchard of the Burchell Nursery, Inc. and which is located at Clovis Avenue and Highway 99 near of Town of Fowler, Calif. All major color code designations are by reference to the dictionary of color by Maerz and Paul, 1st Edition, 1930. Common color names and also employed occasionally.

TREE

Size:

*Generally.*—Average as compared to other common peach cultivars.

Productivity: Productive.

Figure: The orignal seedling was trained in a central leader configuration with moderate spread in the crown of the tree. The tree is generally considered to be upright, to upright spreading in form.

Height: The original seedling had a height dimension of 13.5 feet (4.11 meters) at the end of 1993 growing season.

Width: The original seedling tree had a 5.5 foot width dimension (1.67 meters) at the end of the 1993 growing season.

Current season growth: The current season growth for the new variety was approximately 3.5 to 4.5 feet (1.06–1.37 meters).

Regularity of bearing: Regular, and considered hardy under typical central San Joaquin Valley climatic conditions.

TRUNK

Thickness: Approximately 3.75 inches (95.2 millimeters) in diameter when measured at a distance of approximately six inches (152.4 millimeters) above ground level, at the end of 1993 growing season.

Bark texture: Considered moderately rough with numerous folds of papery scarf skin being present.

Lenticels: Numerous flat, oval lenticels are present. The lenticels range in size from approximately 3 to 7 millimeters in width and from aproximately 1 to 2 millimeters in height.

Bark coloration: Variable, but it is generally considered to be a grey-brown (7-A-8 to approximately 7-C-10).

BRANCHES

Size: Considered medium for the variety.

Thickness: Average as compared to other varieties.

Surface texture: Average, and appearing slightly russetted and furrowed especially on wood which is two years or older.

Current season shoots:

*Surface texture.*—Substantially glabrous.

*Internode length.*—When measured on recumbant fruiting hangerwood, is approximately 12 to 25 millimeters.

*Color of mature branches.*—Medium brown, (approximately 15-H-12 to approximately 8-J-12).

*Color.*—Light green (approximately 19-J-6) with some red coloration appearing on exposed exterior shoots, (approximately 4-F-9). The color of new shoot tips is considered a bright and shiny green (approximately 19-L-6).

LEAVES

Size: Considered relatively large for the species. Leaf measurements have been taken from vigorous upright current season shoots.

*Leaf length.*—Approximately 18 to 20.7 centimeters.

*Leaf width.*—Approximately 4.2 to 5.2 centimeters.

Leaf thickness: Considered average for the variety.

Leaf form: Lanceolate.

Leaf tip form: Acuminate. The tip often appears reflexed downwards and twisted slightly sideways.

Leaf color:

*Upper surface.*—Green, (approximately 23-L-7).

*Lower surface.*—A lighter grey-green, (approximately 21-H-5).

*Mid-vein.*—Color — The color of the mid vein on the lower leaf surface is quite prominant, and is considered a very pale green-yellow, (approximately 18-I-3).

Leaf margins:

*Form.*—Crenate.

*Uniformity.*—Uniform, and having broad, low crenations whcih are generally tipped with brown colored trichomes (this color is not distinctive, however). Occasionally, double crenations are seen near mid margin. The leaf margins, as a general matter, are considered moderately undulate.

Leaf petioles:

*Size.*—Medium.

*Length.*—Approximately 10 to 13 millimeters.

*Thickness.*—Approximately 1.5 to 2.2 millimeters.

*Color.*—Pale green, (approximately 19-J-5). Although this color may be darker when viewed on, and within, the petiole groove, (approximately 20-K-4).

Leaf glands:

*Size.*—Considered medium to large for the species, although there is some variability in the form of same.

*Numbers.*—Approximately 1 to 4 glands can be located on the leaf petiole near the base of the leaf margin.

*Type.*—These glands appear slightly stalked and are most often characterized as reniform in shape, although globose shaped leaf glands are not uncommon. Additionally, 1 to 3 additional leaf glands can be located on the basal portion of the leaf margin. These glands are most often reniform in shape, although globose types are not uncommon.

*Position.*—Considered alternate.

*Color.*—When young, the leaf glands are a bright shiny green, (approximately 20-L-3), however, these leaf glands become darker with advancing senescence.

Leaf stipules:

*Size.*—Medium for the variety.

*Length.*—Approximately 6 to 11 millimeters.

*Form.*—Considered linear lanceolate in form, and having a serrate shaped margin.

*Color.*—Green when young, (approximately 19-K-6), and eventually becoming rust colored with advancing senescence, (approximately 12-C-8). The leaf stipules are considered early deciduous.

FLOWERS

Flower buds:

*Generally.*—The floral buds are considered to be medium in size, conic in form, and slightly appressed relative to the bearing stem.

*Color.*—The bud scales are grey-brown, (approximately 15-A-8). The buds are considered hardy under typical central San Joaquin Valley climatic conditions.

Blooming type: Considered average in relation to other peach cultivars commonly growing in the central San Joaquin Valley. Date of full bloom was Mar. 6, 1994.

Flower type: The variety is considered to be a showy type flower.

Flower size: Diametrical dimensions at full expansion, approximately 40 to 48 millimeters.

Bloom quantity: Considered abundant.

Flower bud frequency: Normally 1 to 2 buds appear per node, although most commonly 2 appear.

Petal size:

*Generally.*—Considered large for the species.

*Length.*—Approximately 18 to 24 millimeters.

*Width.*—Approximately 16 to 22 millimeters.

Petal form: Broadly ovate.

Petal count: Nearly always 5.

Petal color: Light pink when young, (approximately 1-C-7) and darkening with advancing senescence to a medium pink (1-E-7). At maturity, the petal color assumes a dark rose color basally (1-B-4).

Petal claw:

*Form.*—The claw is considered truncate in shape and has a medium size when compared with other similar varieties.

*Length.*—Approximately 1.5 to 2 millimeters.

*Width.*—Approximately 1 millimeter.

Petal margins:

*Generally.*—Considered variable, from nearly smooth, to highly undulate and ruffled, especially apically. Most commonly the undulations are considered moderate.

Petal apex:

*Generally.*—The petal apices appear slightly domed and occasionally notched.

Flower pedicel:

*Length.*—Considered short, and having an average length of approximately 1 to 1.5 millimeters.

*Thickness.*—Considered average, approximately 1 millimeter.

*Color.*—Shiny green, (approximately 20-L-4).

*Surface texture.*—Glabrous.

Floral nectaries:

*Color.*—Dull, orange, (approximately 11-E-12). The color nectaries become more dull, and slightly darker with advancing senescence.

Calyx:

*Surface texture.*—Generally glabrous, and quite rugose.

*Color.*—A dull maroon, (approximately 7-H-3) and often streaked with green, (approximately 21-K-6).

Sepals:

*Surface texture.*—The surface has a medium length, wooly, grey colored pubescence.

*Size.*—Average, and narrowly ovate in form.

*Color.*—A dull maroon, (approximately 7-H-3) and further being streaked with green, (approximately 21-K-6). This green coloration often appears along the sepal margins.

Anthers:

*Generally.*—Average in size.

*Color.*—Red, to reddish-orange dorsally (approximately 4-I-11), and having a darker red color along the marginal edges (4-K-11). It further has a buff color ventrally (approximately 11-H-4), with reddish margins, (approximately 4-H-11).

*Pollen production.*—Pollen is abundant, and has a yellow-gold color (9-L-4).

Filaments:

*Size.*—Variable in length, approximately 13 to 16 millimeters. The filaments, as a general matter, are longer than the pistil.

*Color.*—White, (1-A-1), and becoming a darker, dull, rose color with advancing maturity (approximately 4-C-4).

Pistil:

*Generally.*—Average in size.

*Length.*—Approximately 14 to 16 millimeters, including the ovary.

*Color.*—Considered a very pale green when young, (approximately 17-H-2), and becoming slightly more yellowish with advancing senescence.

*Surface texture.*—The variety has a long pale green, to white pubescence. The color is not distinctive, however.

FRUIT

Maturity when described: The present variety of fruit is described as it would be found in its firm ripe condition at full commercial maturity. In this regard, the fruit of the present variety was first picked on Sep. 4, 1993. The date of last pick of the same fruit in 1993 was approximately September 20 under the ecological conditions prevailing in the San Joaquin Valley of central California.

Size:

*Generally.*—Large, and considered uniform.

*Average cheek diameter.*—Approximately 72 to 79 millimeters.

*Average suture diameter.*—Approximately 74 to 79 millimeters.

*Average axial diameter.*—Approximately 64 to 70 millimeters.

Fruit form:

*Generally.*—Oblate in its lateral aspect, and variable in form in its apical aspect, that is, it is occasionally globose to oval in shape. The fruit is usually asymmetrical with one half of the fruit being larger than the other half.

Fruit suture:

*Generally.*—The suture appears as a thin line which extends from the base to the apex, and appears slightly deeper, basally, within the cavity basin, and apically near the pistil point. As a general matter, no callousing or stitching is evident along the suture line.

Suture:

*Color.*—The suture normally is the same color as the underlying blush. When the suture is underlain with a yellow, ground color, the suture takes on a light orange-red color, (approximately 3-C-11) but on some occasions, especially apically, no red coloration is evident.

Ventral surface:

*Form.*—Variable from relatively smooth to slightly raised, and lipped.

Stem cavity:

*Size.*—Considered medium for the species, and relatively broad.

*Width.*—Approximately 29 to 32 millimeters.

Length: Approximately 30 to 35 millimeters.

Depth: Approximately 10 to 14 millimeters.

Form: Considered oval in its broad outline. As a general matter, a shallow groove can often be located in the cavity shoulders when the fruit was pressed into the accompanying bearing branch.

Fruit base:

*Generally.*—Considered truncate in form. The fruit base, as a general matter, is most frequently slightly, obliquely oriented relative to the fruit axis.

Fruit apex:

*Generally.*—Considered depressed and usually recessed below the height of the apical shoulders. As a general matter a distinct depression is usually evident along the suture line on both the ventral and dorsal sides of the apex. Further, the pistil point is most frequently apical.

Fruit stem:

*Generally.*—Considered relatively short, approximately 8 to 9.5 millimeters in length.

*Thickness.*—Approximately 3 to 4.5 millimeters.

*Color.*—Generally a pale, yellow-green, (approximately 12-L-1).

Fruit skin:

*Generally.*—Considered medium or average in thickness.

*Surface texture.*—The variety has very short pubescence.

*Skin acidity.*—Considered neutral.

Tenacious to flesh: Yes, at commercial maturity.

Tendency to crack: Not observed.

Skin color:

*Generally.*—Variable, with approximately 50% to 80% of the fruit surface covered with an attractive red blush and further having areas of solid, washed color and other areas which are striped and dappled.

Blush color: The blush color is more prevalent basally. This red blush color ranges from a dark garnet red, (approximately 6-L-11) to a lighter orange red, (approximately 3-J-11) with many degrees of shading therebetween. An inspection of the fruit reveals that the darkest areas normally appear basally, and the lighter blush areas are usually found laterally in dappled and striped patterns. Infrequently, small yellowish dots will be seen especially over the solid blushed areas basally.

Skin ground color: This is generally present in variable percentages covering from approximately 15% to approximately 50% of the fruit's surface, and which is golden yellow, (approximately 10-K-6). Some greenish tint can occasionally be retained over the ground color until the date of full maturity.

Flesh color:

*Generally.*—Considered uniform, and a bright golden-yellow, (approximately 10-L-6). The color is substantially continuous from the skin inwardly towards the stone.

Flesh fibers:

*Generally.*—Present and considered numerous and light colored. These fibers are present throughtout the flesh.

Stone cavity:

*Color.*—Red-maroon [7-L-9] and having some red streaking extending outwardly from the stone cavity approximately 5 to 11 millimeters into the flesh. This streaked color is slightly lighter than the color of the stone cavity, (approximately 6-L-10). With advancing senescence, a small amount of red flecking may occasionally appear in the flesh, (approximately 6-L-11).

Flesh texture:

*Generally.*—The flesh is considered firm and fine at commercial maturity. The fruit becomes moderately juicy with advancing senescence.

Ripening: p2 *Generally.*—The fruit of the present variety ripens evenly.

Flavor: Considered sweet and having mild acidity. The flavor is considered balanced and pleasant.

Aroma: Mild and pleasant.

Eating quality:

*Generally.*—Considered very good and well above average considering the date of maturity.

STONE

Attachment:

*Generally.*—The stone is considered a full freestone peach at commercial maturity. Further, very little air space is present around the stone.

Stone size:

*Generally.*—Medium to small.

Length: Approximately 32 to 35 millimeters.

Width: Approximately 24 to 28 millimeters.

Thickness: Approximately 18 to 20 millimeters.

Fibers:

*Generally.*—A Few medium length fibers are attached basally on both the ventral and dorsal sutures.

Stone form:

*Generally.*—The stone form is considered somewhat variable and having a broadly ovate, to occasional nearly oval form.

Stone base: The stone base is generally considered truncate in form.

Base angle: The base angle is variable, however, it is most frequently considered slightly oblique to the stone axis.

Hilum:

*Generally.*—Considered medium in size, and is relatively well defined. The hilum is surrounded with a thick collar which is approximately 2.5 to 4.5 millimeters in thickness.

*Form.*—Considered oval.

Apex:

*Shape.*—The stone apex is raised and has an acute tip.

Stone shape: Considered variable. The stone is normally unequal although occasionally it may appear nearly equal.

Stone surface:

*Surface texture.*—Generally considered medium in roughness and further having substantial pitting located laterally. Further, substantial grooving is evident over the apical shoulders.

*Ridges.*—Numerous fine ridges are present basally and converge towards the base of the stone.

Ventral edge:

*Width.*—Considered medium, and having a dimension of approximately 5 to 6 millimeters at mid-suture. Further, several coalesced wings are present and converge both apically and basally. Additionally, a low keel is present on the ventral edge and is located basally.

Dorsal edge: The dorsal edge, as a general matter, is characterized by a relatively wide groove which extends from the stone base to a point approximately 11 to 17 millimeters from the apex. The groove is narrow, and the stone is substantially eroded along the apical shoulder thereby forming a substantially concave area along the apical shoulder of the dorsal edge.

Stone color: The color of the dry stone is medium to dark brown, (approximately 8-J-10). The color becomes a lighter brown along the stone suture, (approximately 7-C-11). A moderate amount of purplish-brown staining is present over the stone surface, (approximately 7-L-8). This is most readily apparent along the ventral surface.

Tendency to split: Not observed.

Use: The subject variety "Autumn Flame" is considered to be a late maturing, attractively colored, high quality peach which is suitable for use in both local and long distance shipping.

Keeping quality: Excellent.

Resistance to insects and disease: No particular susceptibilities were noted.

Shipping quality: Above average.

Although the new variety of peach tree herein denominated varietally as "Autumn Flame" possesses the described characteristics when grown under the ecological conditions prevailing in the San Joaquin Valley of central California, it is to be understood that variations of the usual magnitude, and characteristics incident to changes in growing conditions, fertilization, pruning and pest control are to be expected.

Having thus described and illustrated my new variety of peach tree, what is new and claimed and desired to be secured by Letters Patent is:

1. A new and distinct variety of peach tree, substantially as illustrated and described, and which is somewhat similar in its harvesting date to the Carnival variety of peach tree (U.S. Plant Pat. No. 2,144) which matures in approximately the same season, and approximately a week later than the common commercial variety Fairtime (unpatented), but which is distinguished therefrom and characterized principally as to novelty, by producing fruit which are ripe for harvesting and shipment approximately September 4 through September 20 under the ecological conditions prevailing in the San Joaquin Valley of central California, the subject variety producing fruit which have an attractive exterior coloration, are freestone by nature, and further have a firm yellow-colored flesh.

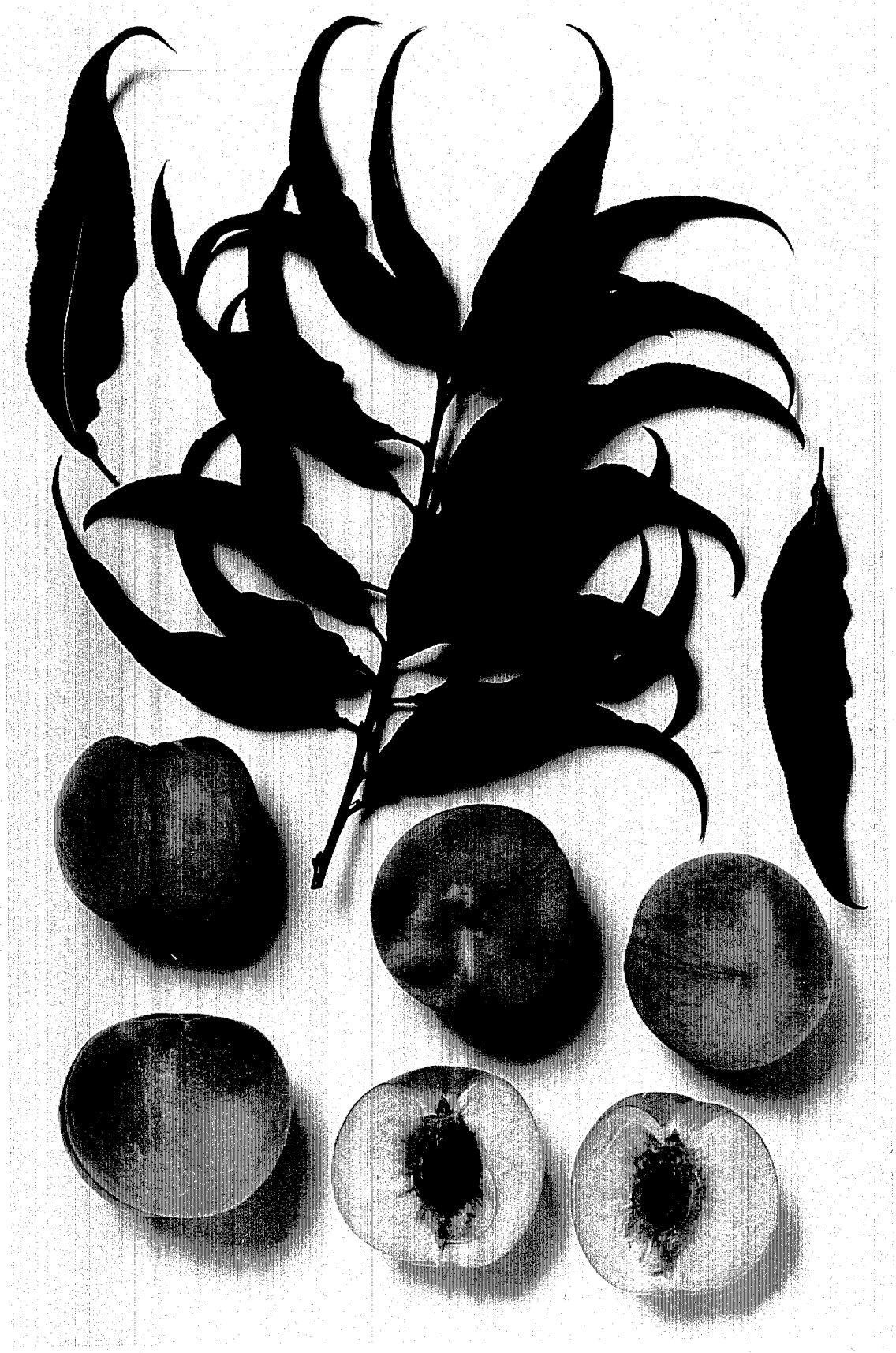

* * * * *